US00PP14002P29

(12) United States Plant Patent
van den Aardwegh

(10) Patent No.: US PP14,002 P2
(45) Date of Patent: Jul. 22, 2003

(54) DODECATHEON PLANT NAMED 'APHRODITE'

(75) Inventor: Kees van den Aardwegh, Hillegom (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,961

(22) Filed: May 6, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Dodecatheon plant named 'Aphrodite', characterized by its upright and tall growth habit; long leaves; and large red purple flowers on long and thick scapes.

1 Drawing Sheet

BOTANICAL CLASSIFICATION/CULTIVAR DESIGNATION

*Dodecatheon L.* cultivar Aphrodite.

BACKGROUND OF THE INVENTION

The present Invention relates to a new and distinct cultivar of Dodecatheon plant, botanically known as *Dodecatheon L.,* and hereinafter referred to by the name 'Aphrodite'.

The new cultivar originated from a random cross-pollination of two unidentified selections of *Dodecatheon L.,* not patented, in Hillegom, The Netherlands. The new cultivar was discovered and selected by the Inventor as a flowering plant within the progeny from this cross-pollination in a controlled environment in Hillegom, The Netherlands, in 1990.

Asexual reproduction of the new cultivar by root divisions taken in Hillegom, The Netherlands, since 1990, has shown that the unique features of this new Dodecatheon are stable and reproduced true to type in successive generations.

SUMMARY OF THE INVENTION

Plants of the cultivar Aphrodite have not been observed under all possible environmental conditions. The phenotype may vary somewhat with variations in environment such as temperature and light intensity without, however, any variance in genotype.

The following traits have been repeatedly observed and are determined to be the unique characteristics of 'Aphrodite'. These characteristics in combination distinguish 'Aphrodite' as a new and distinct cultivar of Dodecatheon:

1. Upright and tall growth habit.
2. Long leaves.
3. Large red purple flowers on long and thick scapes.

Plants of the new Dodecatheon differ primarily from plants of the unidentified parent selections primarily in plant size, leaf size, flower size, scape thickness and flower color.

Plants of the new Dodecatheon can be compared to plants of the Dodecatheon cultivar Queen Victoria, not patented. In side-by-side comparisons conducted in Hillegom, The Netherlands, plants of the new Dodecatheon differed from of the cultivar Queen Victoria in the following characteristics:

1. Plants of the new Dodecatheon were taller than plants of the cultivar Queen Victoria.
2. Plants of the new Dodecatheon had longer and thicker scapes than plants of the cultivar Queen Victoria
3. Plants of the new Dodecatheon had larger flowers than plants of the cultivar Queen Victoria.
4. Plants of the new Dodecatheon had red purple-colored flowers whereas plants of the cultivar Queen Victoria had pink-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Dodecatheon. The photograph comprises a side perspective view of a typical flowering plant of 'Aphrodite'.

DETAILED BOTANICAL DESCRIPTION

In the following description, color references are made to The Royal Horticultural Society Colour Chart, 2001 Edition, except where general terms of ordinary dictionary significance are used. Plants used for the photograph and the following description were about one year old and were grown in an outdoor nursery in Hillegom, The Netherlands. The following measurements and values represent averages taken from a group of typical flowering plants during the early summer.

Botanical classification: *Dodecatheon L.* cultivar Aphrodite.
Parentage:
*Female, or seed, parent.*—Unidentified selection *Dodecatheon L.,* not patented.
*Male, or pollen, parent.*—Unidentified selection of *Dodecatheon L.,* not patented.
Propagation:
*Type.*—By root divisions.
*Root description.*—Numerous, fine.

Plant description:

*Form.*—Perennial flowering scapose plant; upright and tall plant habit. Plants have a basal rosette of leaves with typically a single scape bearing an umbel of nodding single flowers. Moderately vigorous growth habit.

*Plant height* (*length*).—About 50 cm.

*Plant diameter.*—About 30 cm.

*Foliage description.*—Arrangement: Basal rosette of about 15 single sessile leaves. Length: About 15 cm. Width: About 4.6 cm. Shape: Oblanceolate. Apex: Acute to obtuse. Base: Cuneate; sessile. Margin: Entire; slightly undulate. Texture, upper and lower surfaces: Glabrous; leathery. Venation pattern: Pinnate. Color: Developing leaves, upper surface: 138A. Developing leaves, lower surface: 138A to 138B. Fully expanded leaves, upper surface: 138A. Fully expanded leaves, lower surface: 138B. Venation, upper surface: 138A. Venation, lower surface: 143D.

Flower description:

*Flower type and habit.*—Single nodding flowers arranged on terminal umbels; about 25 developing and fully opened flowers per umbel. Flowers not persistent.

*Natural flowering season.*—Late spring to early summer in Hillegom, The Netherlands.

*Flower longevity on the plant.*—About one to two weeks.

*Fragrance.*—Faint; sweet.

*Inflorescence height.*—About 10 cm.

*Inflorescence diameter.*—About 10 cm.

*Flower shape.*—Rotate, corolla and calyx lobes reflexed.

*Flower diameter.*—About 2 cm.

*Flower depth* (*height*).—About 3.5 cm.

*Flower buds.*—Length: About 1.5 cm. Diameter: About 5 mm. Shape: Narrowly ovoid. Color: 143A.

*Petals.*—Quantity per flower: About five; fused at the base; lobes reflexed. Length: About 2.2 cm. Width: About 1.2 cm. Shape: Obovate. Apex: Obtuse. Base: Fused. Margin: Entire. Texture, upper and lower surfaces: Smooth; glabrous. Color: When opening, upper and lower surfaces: N74A to N78A. Fully opened, upper and lower surfaces: N78C; towards the apex, N78B.

*Sepals.*—Quantity per flower: About five; fused at the base; lobes reflexed. Length: About 6 mm. Width: About 7 mm. Shape: Lanceolate. Apex: Acute. Base: Fused. Margin: Entire. Texture, upper and lower surfaces: Smooth, glabrous. Color: When and fully opened, upper surface: 143A; base, 13A to 13B forming a yellow-colored ring at base of flower. When and fully opened, lower surface: 143A.

*Scape.*—Length: About 45 cm. Diameter: About 7 mm. Strength: Moderately strong to strong. Angle: Erect. Color: 144A.

*Pedicels.*—Length: About 6 cm. Diameter: About 1.5 mm. Strength: Moderately strong to strong. Angle: About 5 to 40° from vertical. Color: 144A.

*Preproductive organs.*—Stamens: Quantity per flower: About five. Anther shape: Oblong. Anther length: About 9 mm. Anther color: 161 A to 161 B. Amount of pollen: Abundant. Pollen color: 8A. Pistils: Quantity per flower: One. Pistil length: About 1.2 cm. Stigma shape: Club-shaped. Stigma color: Close to 155A. Style length: About 1.1 cm. Style color: Towards the base, 144D; towards the apex, 187A to 187B. Ovary color: 144B to 144C.

*Fruit.*—Quantity per plant: About 25. Type: Capsule. Length: About 8 mm. Diameter: About 4 mm. Color: Close to 200B.

*Seed.*—Quantity per fruit: About 50. Length: Less than 0.2 mm. Diameter: Less than 0.2 mm. Color: Close to 200B.

Disease/pest resistance: Plants of the new Dodecatheon have not been noted to be resistant to pathogens and pests common to Dodecatheon.

Weather tolerance: Plants of the new Dodecatheon have been observed to be tolerant to rain and wind and tolerant to temperatures from −20 to 35° C.

It is claimed:

1. A new and distinct cultivar of Dodecatheon plant named 'Aphrodite', as illustrated and described.

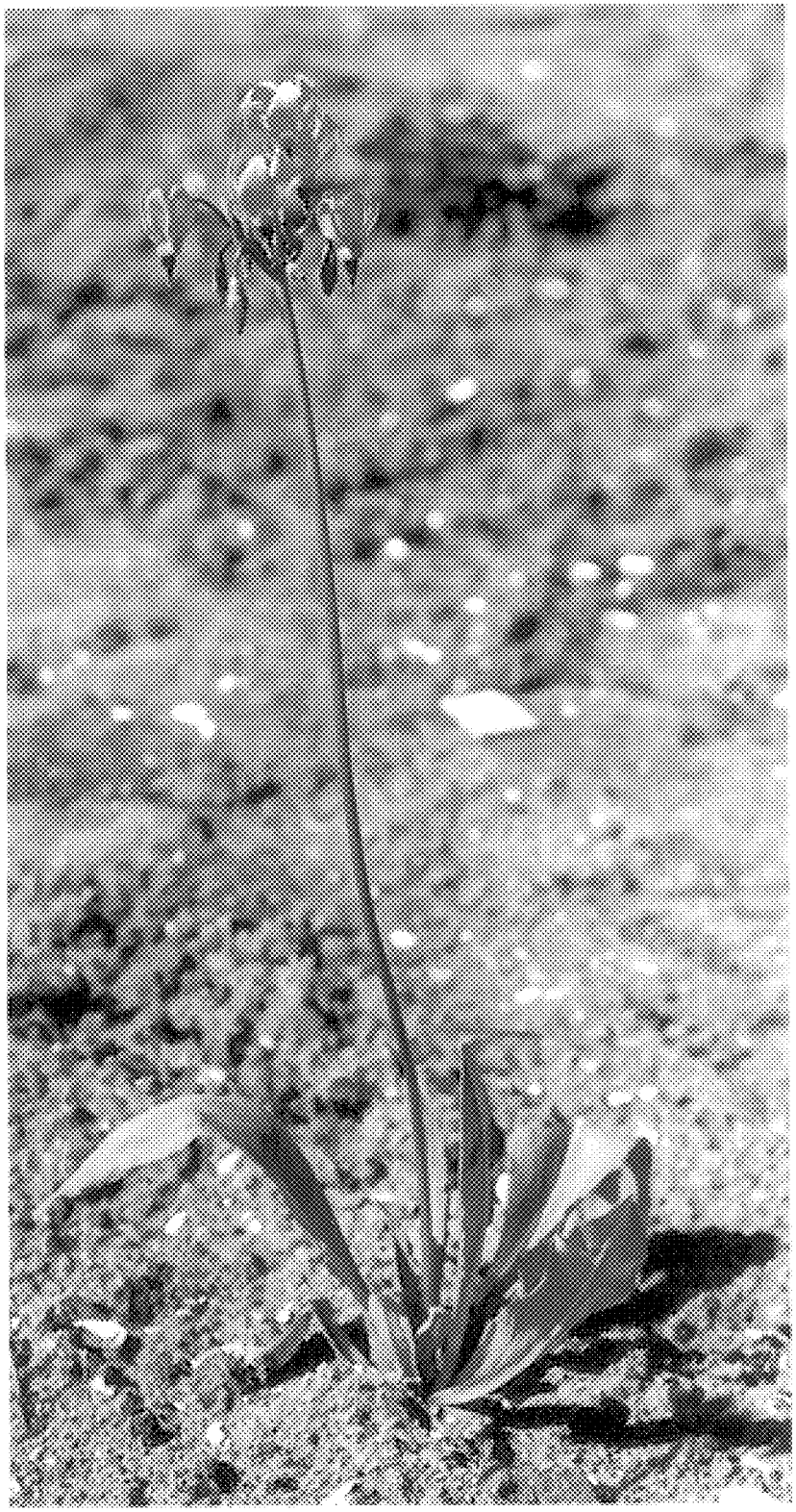

* * * * *